(12) United States Patent
Johnson et al.

(10) Patent No.: US 6,874,353 B2
(45) Date of Patent: Apr. 5, 2005

(54) YIELD POINT ADAPTATION FOR ROTATING VISCOMETERS

(75) Inventors: Johnny W. Johnson, Duncan, OK (US); Ronnie G. Morgan, Waurika, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 223 days.

(21) Appl. No.: 10/354,846

(22) Filed: Jan. 30, 2003

(65) Prior Publication Data

US 2004/0149019 A1 Aug. 5, 2004

(51) Int. Cl.⁷ .......................... G01N 11/14; G01N 11/16
(52) U.S. Cl. ..................... 73/54.28; 73/54.31; 73/54.38
(58) Field of Search ............................. 73/54.28, 54.31, 73/54.33, 54.34, 54.38

(56) References Cited

U.S. PATENT DOCUMENTS

| | | | |
|---|---|---|---|
| 2,096,222 A | 10/1937 | Bock | |
| 2,122,765 A | 7/1938 | Weiler | ........................ 73/54.03 |
| 2,237,743 A | 4/1941 | McIntyre | |
| 2,266,733 A | 12/1941 | Bays et al. | |
| 2,626,786 A | 1/1953 | McGlothlin | ..................... 259/8 |
| 2,953,016 A | 9/1960 | Seitz, Jr. | |
| 2,992,651 A | * 7/1961 | Krofta | ......................... 137/92 |
| 3,027,756 A | 4/1962 | Head | |
| 3,053,079 A | 9/1962 | Miller et al. | |
| 3,269,171 A | 8/1966 | Bruss et al. | |
| 3,285,057 A | 11/1966 | De Zurik | |
| 3,292,423 A | 12/1966 | Banks | |
| 3,347,089 A | 10/1967 | Perry | |
| 3,402,729 A | 9/1968 | Richmond et al. | |
| 3,435,666 A | 4/1969 | Fann | |
| 3,587,295 A | 6/1971 | Simons | |
| 3,636,753 A | 1/1972 | Thiele et al. | |
| 3,751,975 A | 8/1973 | Katusra | |
| 3,803,903 A | 4/1974 | Lin | |
| 3,875,791 A | 4/1975 | Fitzgerald et al. | |

(Continued)

FOREIGN PATENT DOCUMENTS

| | | |
|---|---|---|
| BE | 839479 | 9/1976 |
| CA | 672380 | 10/1963 |
| DE | 1184119 | 12/1964 |
| RU | 415553 | 7/1974 |
| RU | 568869 | 11/1977 |
| RU | 594438 | 2/1978 |
| RU | 670855 | 6/1979 |

OTHER PUBLICATIONS

U.S. patent application Ser. No. 09/499,827, filed Feb. 8, 2000 (inventors: Phillip C. Harris, Stanley J. Heath, Ronald J. Powell, Harold G. Walters, Ronnie G. Morgan, Billy F. Slabaugh, David M. Barrick, and Johnny W. Johnson).

(Continued)

*Primary Examiner*—Daniel S. Larkin
(74) *Attorney, Agent, or Firm*—John W. Wustenberg; E. Harrison Gilbert, III (57) ABSTRACT

A conventional Couette viscometer is transformed to measure yield point, also known as yield stress, and other rheology of various fluids, including ones with particulates. A rotating viscometer includes a driven portion, a responsive body, a standard spring, and a plurality of fins. The fins have predetermined shapes such that the rotating viscometer and the standard spring, connected to the responsive body having at least a portion of the fins, are sensitive to detect yield stress of a test fluid composition in response to a selected rotation imparted to the driven portion. A method of measuring yield stress includes operating a standard rotating viscometer modified with a plurality of intermeshing fins such that a standard spring of the standard rotating viscometer responds to a torque that is related to yield stress and that is imposed by a stressed test material on a portion of the fins connected to the spring.

20 Claims, 8 Drawing Sheets

U.S. PATENT DOCUMENTS

| | | | |
|---|---|---|---|
| 4,044,602 A | | 8/1977 | Higgs et al. |
| 4,065,959 A | | 1/1978 | Richardson |
| 4,151,744 A | | 5/1979 | Hemmings |
| 4,157,036 A | | 6/1979 | Kivenson ............... 73/290 R |
| 4,175,425 A | | 11/1979 | Brookfield |
| 4,181,023 A | | 1/1980 | Clamroth et al. |
| 4,184,364 A | | 1/1980 | Du Bae |
| 4,283,938 A | | 8/1981 | Epper et al. |
| 4,299,118 A | | 11/1981 | Gau et al. |
| 4,299,119 A | * | 11/1981 | Fitzgerald et al. ......... 73/54.28 |
| 4,341,111 A | | 7/1982 | Husar |
| 4,448,061 A | | 5/1984 | Brookfield |
| 4,466,276 A | | 8/1984 | Ruyak et al. |
| 4,484,468 A | | 11/1984 | Gau et al. |
| 4,499,753 A | | 2/1985 | Carr |
| 4,501,143 A | | 2/1985 | Prior et al. |
| 4,510,800 A | | 4/1985 | Prior |
| 4,557,142 A | * | 12/1985 | Hensley et al. .......... 73/152.19 |
| 4,571,988 A | | 2/1986 | Murphy, Jr. |
| 4,612,800 A | | 9/1986 | Erian |
| 4,622,846 A | | 11/1986 | Moon, Jr. et al. |
| 4,648,264 A | | 3/1987 | Freese et al. |
| 4,653,313 A | | 3/1987 | Sabins et al. ............. 73/54.39 |
| 4,668,911 A | | 5/1987 | Mueller et al. |
| 4,823,594 A | | 4/1989 | Gray |
| 4,829,811 A | | 5/1989 | Ehlert et al. |
| 4,879,897 A | | 11/1989 | Booth et al. |
| 5,167,143 A | | 12/1992 | Brookfield |
| 5,301,541 A | * | 4/1994 | Joseph et al. ............. 73/54.32 |
| 5,321,974 A | | 6/1994 | Hemmings et al. |
| 5,546,791 A | | 8/1996 | Meeten |
| 5,684,247 A | | 11/1997 | Preikschat |
| 5,799,734 A | | 9/1998 | Norman et al. |

OTHER PUBLICATIONS

K.L. Mackey, R.G. Morgan and J.F. Steffe, "Effects of Shear–Thinning Behavior on Mixer Viscometry Techniques," submitted to Journal of Texture Studies, Michigan Agricultural Experiment Station, Journal Article No. 12280, pp. 1–17 (Apr. 1, 1987).

Publication entitled "TT100 In–Line Viscometer," 5 pp., Brookfield Engineering Laboratories, Inc., Stoughton, Mass. (Sep. 1988).

Publication entitled "TT200 Process Viscometer," 4 pp., Brookfield Engineering Laboratories, Inc., Stoughton, Mass. (Jun. 1990).

Document entitled "Description of Stirring Chamber," 5 pp. (believed to be published or to disclose device used or sold prior to Jan. 1999).

Schematic drawing entitled "Modified GAS–CHEK™ Slurry Cup," High Pressure Consistometer, p. 9, Halliburton Services (believed to be published or to disclose device used or sold prior to Jan. 1999).

Publication entitled "Cement Slurry Measurement Instruments For Laboratory," 1 p., Halliburton Services (believed to be published prior to Jan. 1999).

Publication entitled "Cement Measuring and Testing Instruments," 2 pp., Halliburton Services (believed to be published prior to Jan. 1999).

J.R. Cameron, D.C. Gardner and R.W. Veatch, Jr., "New Insights on the Rheological Behavior of Delayed Crosslinked Fracturing Fluids," SPE 18209, Society of Petroleum Engineers (1988).

F.L. Sabins, J.M. Tinsley, and D.L. Sutton, "Transition Time of Cement Slurries Between the Fluid and Set State," SPE 9285, Society of Petroleum Engineers (1980).

Publication entitled "Oil Well Cement Testing Equipment, Atmospheric Pressure Consistometer," 2 pp., Chandler Engineering Co., Tulsa, Okla. (1982).

Publication entitled "RheoChan Rotational Rheometer, Model 7400," 6 pp., EG&G Chandler Engineering, Tulsa, Okla. (believed to be published prior to Jan. 1999).

Publication entitled "Nowsco News, Compact Pressurized Consistometer," 2 pp., Nowsco Well Service Ltd., Calgary, Alberta, Canada (believed to be published prior to Jan. 1999).

Publication entitled "Section 8, Thickening Time Tests,"pp. 22–28, American Petroleum Institute (believed to be published prior to Jan. 1999).

* cited by examiner

YIELD POINT ADAPTATION FOR ROTATING VISCOMETERS

BACKGROUND OF THE INVENTION

This invention relates generally to determining the yield point, also known as yield stress, of a fluid as well as conventional shear stress versus shear rate viscosity data. More particularly, this invention relates to adapting a conventional bob and sleeve viscometer to provide direct measurement of a material's yield stress.

Ascertaining rheological properties of fluids used in drilling and completing oil and gas wells normally requires that "shear stress-shear rate" data (referred to as "rheogram data") be collected via a viscometric device. Then by selecting an a priori viscosity model, the data can be analyzed, usually by statistical means, to determine "best fit" model parameters that are the quantitative estimates for specific rheological properties, including yield stress. Common models used in the oil and gas industry include:

Newtonian fluid, defined as:

$$\mu = \left[\frac{\tau}{\gamma}\right] = \text{constant} \quad [1]$$

Power Law, defined as:

$$\eta_{PL} = \left[\frac{\tau}{\gamma}\right] = K_p(\dot{\gamma})^{n_p - 1} \quad [2]$$

Bingham Plastic, defined as:

$$\eta_{BP} = \left[\frac{\tau}{\dot{\gamma}}\right] = \left[\frac{YP}{\dot{\gamma}}\right] + PV \quad [3]$$

Herschel-Bulkley, defined as:

$$\eta_{HB} = \left[\frac{\tau}{\dot{\gamma}}\right] = \left[\frac{\tau_0}{\dot{\gamma}}\right] + K_{HB}(\dot{\gamma})^{n_H - 1} \quad [4]$$

Robertson-Stiff, defined as:

$$\eta_{RS} = \left[\frac{\tau}{\dot{\gamma}}\right] = \frac{[A(C + \dot{\gamma})^B]}{\dot{\gamma}} \quad [5]$$

where: $\eta$=apparent viscosity; $\tau$=viscometric shear stress; $\gamma$=viscometric shear rate; $\mu$=Newtonian viscosity coefficient; $\eta_{PL}$=apparent viscosity for power law model; $K_p$=power law consistency coefficient=apparent viscosity at shear rate of unity; $n_p$=power law shear thinning index; $\eta_{BP}$=apparent viscosity for Bingham Plastic model; YP=Bingham Plastic yield point; PV=Bingham Plastic viscosity coefficient; $\eta_{HB}$=apparent viscosity for Herschel-Bulkley model; $K_{HB}$=Herschel-Bulkley consistency coefficient; $n_H$=Herschel-Bulkley shear thinning index; $\tau_0$=yield stress or yield point for Herschel-Bulkley fluid; $\eta_{RS}$=apparent viscosity for Robertson-Stiff model, and A, B and C are coefficients for the Robertson-Stiff model. Note that the quantity $A(C)^B$ equates to the yield stress of the material.

In most cementing applications and many drilling fluids, it is necessary to deploy a rheological model that accommodates a finite "yield stress", often referred to as the yield point (YP). The YP is the threshold shear stress that must be applied to create flow of a fluid. Yield stress or yield point of drilling muds and cementing fluids directly affects their performance. For example, yield stress/yield point of a fluid directly impacts the conditions under which laminar flow becomes turbulent. For a drilling mud, it relates to the mud's ability to transport cuttings from the wellbore, for example. In cementing fluids, it relates to the fluid's ability to remove "mud cake" and control gas migration, for example.

The most common viscometer configuration used in measuring rheology of drilling and oil/gas completion fluids is a simple concentric cylinder viscometer (Couette).

Figure 1:
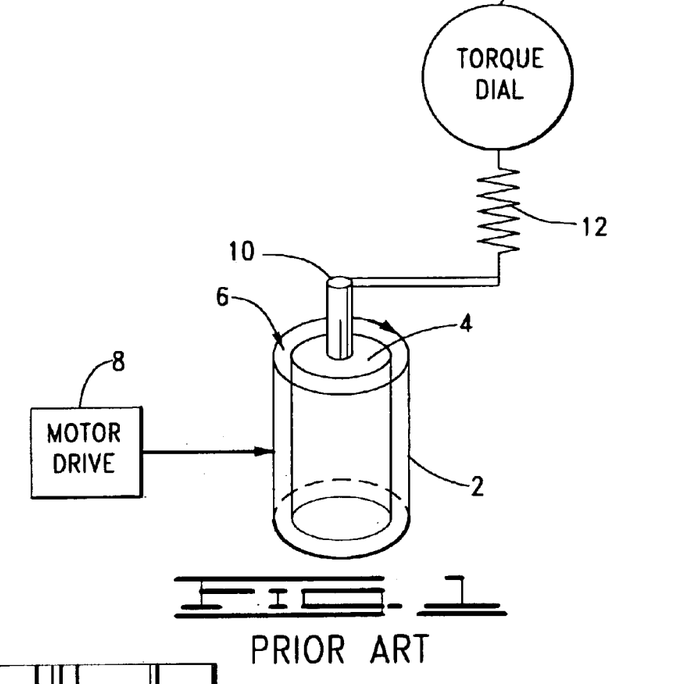
FIG. 1 represents elements of a conventional Couette or rotating viscometer.

Referring to FIG. 1, such a viscometer has an outer cylinder 2, called the "sleeve," with a concentric inner cylinder 4, called the "bob." The sleeve 2 fits concentrically around the outside of the bob 4, leaving a small annular gap 6 in which the fluid sample is received. The sleeve 2 attaches to a motor-driven rotating drive collar (generally shown as motor drive 8) that turns the sleeve 2 at a predetermined rotational speed. In many cases, the bob 4 is a cylinder that has a rod or stem 10 extending from the top. The stem 10 is inserted into a receptacle device that measures torque. The receptacle device of one type of rotating viscometer includes a spring 12. Such a viscometer correlates displacement of the spring 12 caused by rotation of the attached bob 4 with torque being applied to the bob 4 by the fluid sample to which stress is applied by the motor-driven sleeve 2. Torque is indicated by a suitable torque readout, such as a torque dial 14, for example.

In use, the bob/sleeve assembly is lowered into a sample of material until the fluid sample fills a pre-designated portion of the annular gap 6 (the volumetric space between the bob 4 and sleeve 2 over some specified axial distance). A rotational speed is selected and the motor of the motor drive 8 is turned on. The rotating drive collar turns the sleeve 2, which applies a stress to the fluid in the annular gap 6. If the stress is sufficient, the fluid will flow in the rotational direction, applying a resulting stress to the bob 4. The stress applied to the outer surface of the bob 4 creates a torque on the bob 4. This torque is transferred to the spring 12, which moves the viscometer's torque dial 14 that is calibrated in torque units.

Known mathematical formulas can be used in known manner to transform the dimensions of the bob 4 and sleeve 2, along with the rotational speed of the sleeve 2 and the corresponding torque measured by the bob 4 as shown on the torque dial 14, into a set of shear stress and shear rate data.

There are two methods for determining the YP of a fluid: one (called RF, regression fit) is to select a viscosity model a priori, and statistically determine the best fitting parameters; the other method is often referred to as "direct measurement" (DM). In the RF method, a model such as Equation [3], [4] or [5] above is selected, and then statistical regression used to best fit that model to the rheogram data. The American Petroleum Institute (API) has recommended practices for using shear stress and shear rate data for a fluid to ascertain rheological characteristics or parameters, including the yield stress (also referred to as yield point) and plastic viscosity of a Bingham Plastic fluid model. However, the value of YP obtained by curve fitting a predetermined model via a given set of shear stress and shear rate data depends upon which model was selected. Herein lies the problem. The actual yield stress of a fluid is a physical property, and yet common practice in the industry is to transform shear stress and shear rate data into a best fit (regressed) value for yield point. With complex oil field cementing systems, for example, this method can often result in significant error.

Figure 2A:
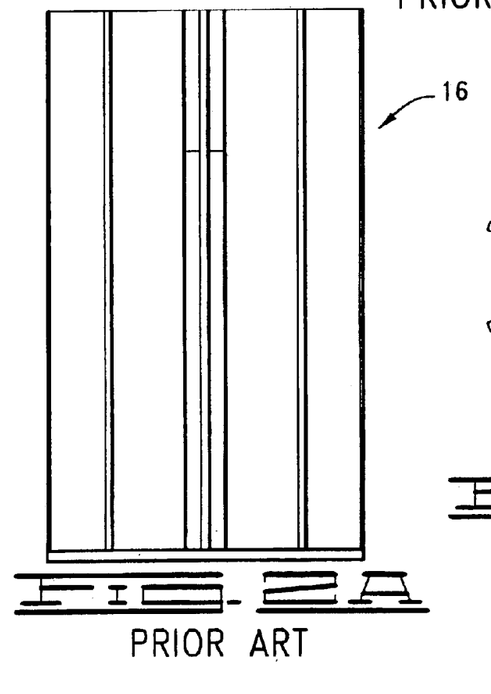
FIGS. 2A and 2B illustrate elevation and end views, respectively, of a ten-blade vane bob for viscometer in which a shaft rotates at some pre-set and constant speed while measuring torque.
Figure 2B:
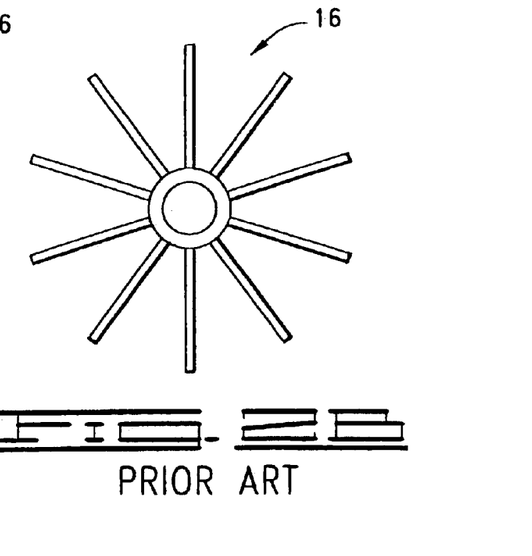

Thus, the DM method is preferred over the RF method. The DM method usually requires very sensitive speed control and torque measuring sensors. The DM method can be further partitioned into two general categories: the YP,i method, being the minimal shear stress required to initiate flow when starting from a stationary condition; while the YP,e method is aimed at measuring the equilibrium stress state that a fluid retains as it comes to rest, after turning off the rotation of the moving cylinder. The YP,i method usually entails measuring the torque versus time profile while starting a viscometer from the "rest position;" this usually requires the ability to rotate the sleeve very slowly, often less than one revolution per minute (rpm). The YP,e method requires the torque decay curve to be carefully monitored after turning off the rotating cylinder. The rotating cylinder will come to rest while the fluid retains an internal stress that is equal to the YP. Due to inertial effects, the rotational speed of both DM methods (YP,i and YP,e) should be below one revolution per minute for most of the oil field type Couette viscometers. These conventional oil field viscometers are, however, not sufficiently sensitive to measure the low torque values for either DM method. Additionally, these field viscometers may not be equipped with the capability of controlling a constant rotational speed less than unity. Error can also be induced by slippage that occurs between the smooth surface of a bob and the fluid, especially when particulates are present. This slippage may cause significant error when measured torques are quite low. To overcome this problem, a vane device (reference page 138 of J. F. Steffe, *Rheological Methods in Food Process Engineering* (1992)), shown in FIGS. 2A and 2B, is often used as an accepted method among those skilled in the art. The purpose of the vanes is to create an "inner cylinder" or bob out of the fluid sample, thus the shearing interface between the bob and sleeve is "fluid-to-fluid", rather than "metal-to-fluid."

Figure 3A:
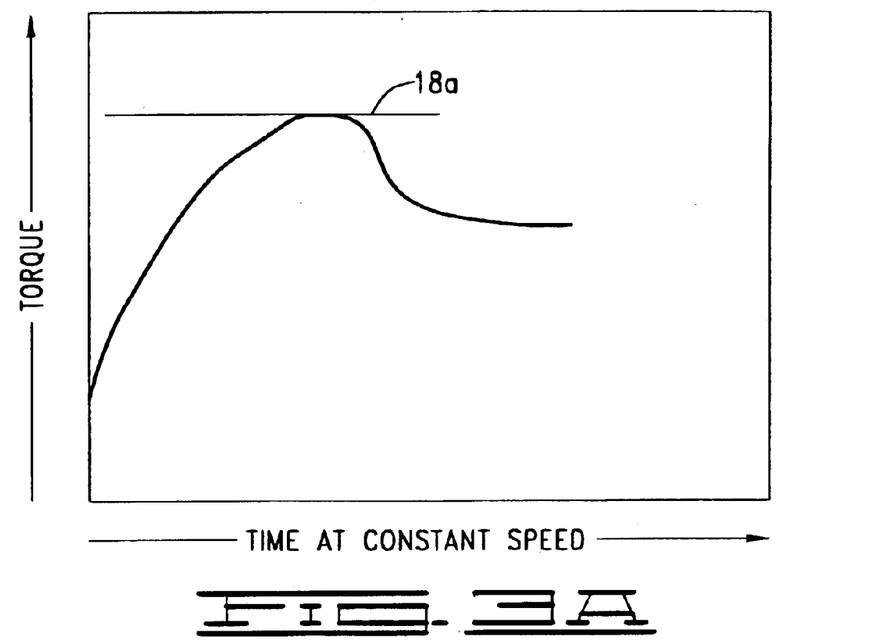
FIG. 3A is a graphical representation of torque versus time curve for the YP,i method for constant speed operation of a viscometer modified with the vane bob of FIGS. 2A–2B.
Figure 3B:
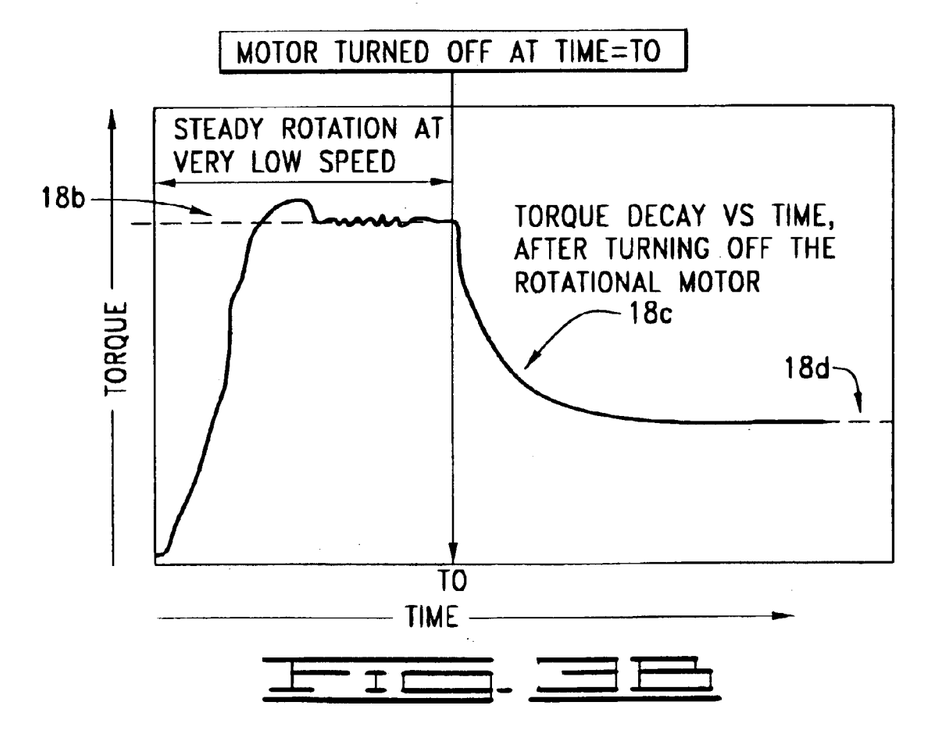
FIG. 3B is a graphical representation of a torque versus time decay curve for the YP,e method.
Figure 3C:
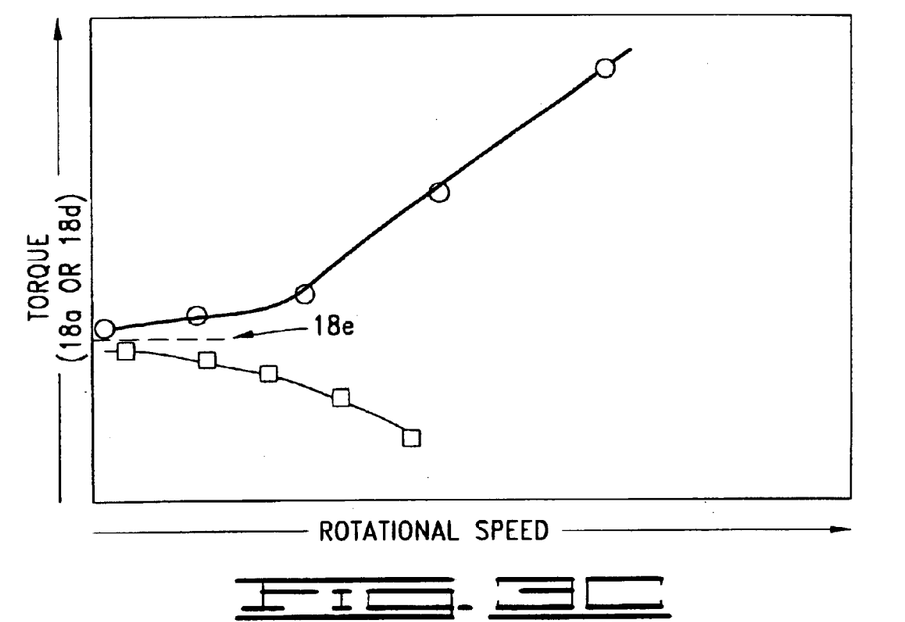
FIG. 3C represents the concept used to correct YP,i and YP,e data for inertial effects.

FIGS. 2A and 2B represent a ten-bladed vane device 16 for directly measuring YP by either the YP,i method or the YP,e method. The vane device 16 connects to the torque sensor of a rotational viscometer and is lowered into the fluid sample as described above for the Couette or rotating viscometer of FIG. 1. In the YP,i method, the rotational speed is set very low (usually less than or equal to one rpm), then the switch is turned on, and torque versus time is monitored until the torque peaks, as shown in FIG. 3A at 18a. The peak torque is converted into a shear stress being applied to the effective circumferential area of the vane's fluid-to-fluid interface using vane device 16. The yield point is computed from the peak torque 18a observed in FIG. 3A, which represents the stress required to initiate flow. The subsequent decline in torque shown by the graph in FIG. 3A implies that flow has been initiated. In the YP,e method, the vane device 16 connects to the torque sensor of a rotational viscometer and is lowered into the fluid sample as described above for the Couette or rotating viscometer of FIG. 1. The rotational speed is set very low (less than or equal to one rpm), then the switch is turned on, and the vane (bob) or sleeve rotates at constant rpm creating a torque versus time curve shown in FIG. 3B. Once equilibrium has been obtained, usually indicated by a constant level or torque, such as line 18b, the device is turned off and the torque versus time decay is recorded, as 18c and 18d observed in FIG. 3B. To ensure that the inertial effects have not significantly contributed to the torque readings in the YP,i and YP,e methods, a common analysis method is to plot the YP,i and YP,e torques, 18a and 18d, respectively, versus three or four of the lowest rotational speeds obtainable, as shown in FIG. 3C. The torque versus rotational speed data should approach an asymptotic value as speed approaches zero, see 18e in FIG. 3C. The asymptote 18e is the torque value to use to compute YP.

However, conventional oil field Couette viscometers have three limitations that prevent their use with a vane device for measuring yield stress: their torque responsive springs are not sensitive enough for accurate detection; many such viscometers are not equipped with capabilities of operating at less than one rpm; and the vane device works best if it is attached to a rotating shaft and lowered into a large sample of fluid, without the use of the outer sleeve. Most oil field viscometers are equipped with their rotational devices connected to the outer cylinder (the sleeve), while the inner cylinder (the bob) remains stationary and connected to the torque spring, as observed in FIG. 1. When attempts were made to adapt the vane in FIGS. 2A and 2B to a typical oil field viscometer, the device was not sensitive enough to detect low levels of YP, such as less than ten pascals (Pa). The problem is the combination of sensitivity of the torque spring and the fact that the vane remains stationary, while the sleeve rotates.

In the case of cements with added particulates and fracturing fluids with proppant, conventional Couette viscometers are not normally capable of accurately measuring rheogram data nor YP due to two key constraints: the, gap between the bob and sleeve is too small, thus particles easily jam and lock-up the viscometer; and the rotation of the sleeve creates centrifugal forces that cause the particles to migrate and stratify in the radial direction. Both of these physical phenomena cause unacceptable error.

Therefore, a device is needed that could readily adapt to conventional oil field Couette type viscometers for providing capabilities to accurately and directly measure YP, as well as rheogram data (shear stress versus shear rate data) for fluids with particles. There is also the need for a simple device that could readily adapt to the current oil field viscometer and measure rheology of particle laden fluids, especially yield stress (yield point) data.

SUMMARY OF THE INVENTION

The present invention provides a cost effective method and apparatus and an adapter that transforms a conventional oil field Couette viscometer into an instrument that can readily and accurately measure yield stress of various fluids, such as but not limited to drilling muds, drill-in fluids, cements, fracturing fluids, foams, emulsions, and the like. It also provides a means of characterizing rheology of complex fluids that contain particulates, such as sand, high density additives for cement, and the like.

An apparatus of the present invention for measuring yield stress of a fluid composition comprises a rotating viscometer including a driven portion, a responsive body, a standard spring, and a plurality of fins, the plurality of fins having predetermined shapes disposed in the rotating viscometer such that the rotating viscometer and the standard spring thereof, connected to the responsive body of the rotating viscometer having at least a portion of the fins thereon, are sensitive to detect yield stress of a test fluid composition in response to a selected rotation imparted to the driven portion of the rotating viscometer.

The present invention also provides a yield stress adapter for a rotating viscometer, which yield stress adapter comprises: a bob including a shaft and two axially spaced groups of circumferentially disposed triangular members connected to the shaft; and a sleeve including a group of circumferentially disposed triangular members connected to an inner surface of the sleeve, the sleeve configured to receive the bob within the sleeve such that the group of triangular members of the sleeve is disposed between the two axially spaced groups of the bob when the bob is received in the sleeve. In a specific implementation, each of the two axially spaced groups of the bob includes a respective set of four right triangular members, one set of which right triangular members has the hypotenuse of each right triangular member thereof extending upwardly and away from the respective hypotenuse's point of contact with the shaft to an upper distal tip and the other of the two sets of which right triangular members has the hypotenuse of each right triangular member thereof extending downwardly and away from the respective hypotenuse's point of contact with the shaft to a lower distal tip; and the group of triangular members of the sleeve includes four right triangular members having the hypotenuse of each right triangular member thereof disposed along the inner surface of the sleeve parallel to an axis of the sleeve such that an apex of each such right triangular member defines an inner distal tip. In another embodiment, the groups of triangular members are switched as to which of the bob and sleeve they are on. The adapter can form part of a yield stress measurement device that also comprises: a motor connected to the sleeve; and a torque sensor connected to the bob.

The present invention also provides a method of measuring yield stress, comprising operating a standard rotating viscometer modified with a plurality of intermeshing fins such that a standard spring of the standard rotating viscometer responds to a torque that is related to yield stress and that is imposed by a stressed test material on a portion of the fins connected to the spring.

A method of modifying a standard rotating viscometer for use in determining yield point in accordance with the present invention comprises modifying a standard rotating viscometer by replacing a standard bob and a standard sleeve of the standard rotating viscometer with a modified bob and a modified sleeve, on which modified bob and modified sleeve are disposed a plurality of intermeshing fins such that a standard spring of the standard rotating viscometer responds to a torque that is related to yield point and that is imposed by a stressed test material on the standard spring through connection of the spring to the modified bob. The present invention more specifically provides a method of converting a Couette viscometer, having a conventional bob, a conventional sleeve, and a standard Couette viscometer spring connected to the conventional bob, to a yield stress measurement device, the method comprising replacing the conventional bob and the conventional sleeve without replacing the standard Couette viscometer spring, including: replacing the conventional sleeve with a modified sleeve having a plurality of fins extending inwardly from an inner surface of the modified sleeve; and replacing the conventional bob with a modified bob, including connecting the modified bob to the standard Couette viscometer spring, the modified bob having two pluralities of fins extending outwardly. Alternatively, the pluralities of fins can be switched such that the two pluralities are on the sleeve and the one plurality is on the bob.

The present invention still further provides a method for using a Couette viscometer to determine yield point, comprising: lowering a modified bob, connected to a standard Couette viscometer spring, and modified sleeve into a test composition; rotating the modified sleeve; and sensing torque through the modified bob and the standard spring, which torque is created by the test composition in response to rotating the modified sleeve.

Therefore, from the foregoing, it is a general object of the present invention to provide novel and improved apparatus and method by which yield stress or yield point can be directly measured or determined. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 9 illustrates conventional viscosity data collected via conventional bob/sleeve and the YPA device.

FIG. 10 illustrates that the YPA device can be used to directly measure the YP of highly concentrated particulate suspensions.

DETAILED DESCRIPTION OF THE INVENTION

The apparatus for measuring yield stress of a fluid composition in accordance with the present invention comprises a rotating viscometer that includes a driven portion, a responsive body, a "standard" (that is, standard for a conventional Couette or rotating viscometer) spring and a plurality of fins or vanes (referred to herein as fins). These fins have predetermined shapes and the fins are disposed in the rotating viscometer such that the rotating viscometer and the standard spring of the rotating viscometer are sensitive to detect yield stress of a test fluid composition in response to a selected rotation imparted to the driven portion of the rotating viscometer. The standard spring of the rotating viscometer is connected to the responsive body of the rotating viscometer, which responsive body has at least a portion of the fins on it. In the illustrated embodiment of FIGS. 4 and 5, a set of intermeshing fins or vanes are attached to a modified bob and modified sleeve that easily attach to existing Couette viscometers common in the oil field service industry, such as but not limited to Fann and Chandler rotating viscometers. The number, shape and position of these triangular fins provide for proper sensitivity with the standard torque springs being used in the Fann 35 and Chandler type viscometers, for example, as well as for allowable clearance between fins sufficient to allow free movement of particles.

The plurality of fins can be disposed in any suitable manner to achieve the yield stress or yield point responsiveness. In general, one or more groups of fins is disposed on the responsive member and one or more groups of fins is disposed on the driven portion of the rotating viscometer. For example, as shown in the particular implementation of FIGS. 4 and 5, the plurality of fins of this embodiment is disposed in three groups. Two of the groups of fins are disposed on the responsive body, and the other of the three groups of fins is disposed on the driven portion such that the fins of such other group are between the two groups of fins disposed on the responsive body. These groupings could be reversed in that the two groups could be disposed on the driven portion and the other of the three groups disposed on the responsive body (this would only change the conversion constant used to convert actual torque (dial readings) to yield stress values in pascals.) In the particular illustrated embodiment, the responsive body is a modified bob 20 that includes a shaft 22 connected to the standard spring inside the receptacle device 24 of the rotating viscometer (which standard spring and receptacle device 24 can be the same as represented in FIG. 1). This shaft 22 has eight fins 26 disposed on it in two axially spaced groups (as indicated by suffixes "a" and "b" to the fin-designating reference numeral 26). The driven portion of the embodiment shown in FIGS. 4 and 5 includes a sleeve 28 modified in that it has four fins 30 disposed on it such that the four fins 30 on the sleeve 28 are between the two axially spaced groups of fins 26a, 26b on the shaft 22 when the shaft 22 is placed inside the sleeve 28 as illustrated in the drawings. FIG. 6 shows an embodiment in which fins 26a', 26b' are on the sleeve 28' and the interposed fins 30' are on the shaft 22'.

The present invention also provides a yield stress measurement device comprising a yield stress adapter, a motor, and a torque sensor. The motor and torque sensor can be of conventional types known in the art, such as represented in FIG. 1. The yield stress adapter includes the respectively illustrated modified sleeve/modified bob configuration previously described.

Figure 4:
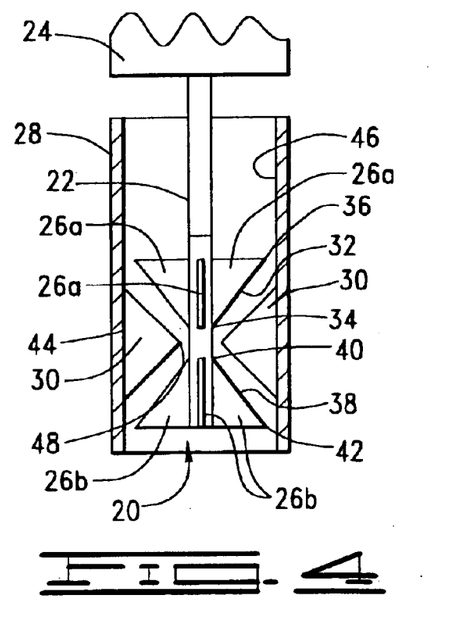
FIG. 4 is a sectioned elevational view of one embodiment of a modified sleeve and bob of a yield stress adapter of the present invention.
Figure 5:
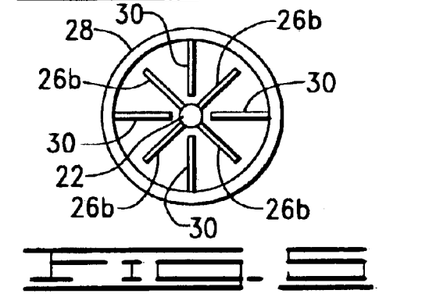
FIG. 5 is an end view of the embodiment shown in FIG. 4.
Figure 6:
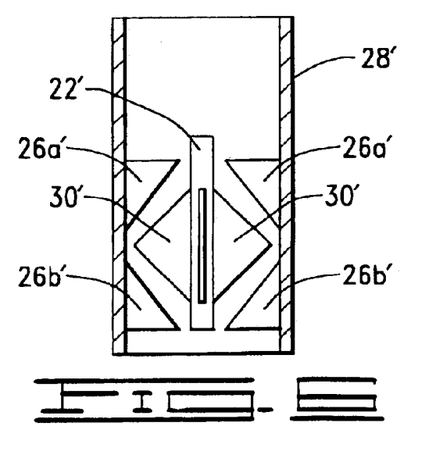
FIG. 6 is a sectioned elevational view of another embodiment of a modified sleeve and modified bob of a yield stress adapter of the present invention.

Referring to the embodiment of FIGS. 4 and 5, each of the two axially spaced groups of fins 26a, 26b connected to the shaft 22 includes a respective set of four right triangular members having two sides of equal length (isosceles). One set of these right triangular members (the group with fins 26 a in FIG. 4) has the hypotenuse 32 of each right triangular member extending upwardly and away from the respective hypotenuse's point of contact 34 with the shaft 22 to an upper distal tip 36. The other of the two sets of these right triangular members (fins 26b in FIG. 4) has the hypotenuse 38 of each right triangular member extending downwardly and away from the respective hypotenuse's point of contact 40 with the shaft 22 to a lower distal tip 42. In the particular implementation shown in these two drawings, the upper distal tips 36 are substantially coplanar, and the lower distal tips 42 are substantially coplanar in a different plane from, but one parallel to, the one of the upper distal tips 36.

The group of triangular members of the sleeve 28 for the embodiment of FIGS. 4 and 5 includes four right triangular members (the fins 30 for FIG. 4) having a hypotenuse 44 of each such right triangular member disposed along inner surface 46 of the sleeve 28 parallel to a longitudinal axis of the sleeve 28 such that an apex of each such right triangular member defines an inner distal tip 48. In the particular implementation illustrated in these drawings, these inner distal tips 48 are substantially coplanar relative to a plane in between and parallel to those of the upper and lower distal tips 36, 42.

In a particular implementation, the shaft 22 has a length of 1.54 inches and each attached right isosceles triangular fin 26 has 0.5-inch orthogonal sides. The nearest points of the group of fins 26a and group of fins 26b are spaced 0.23 inch. The sleeve 28 has a length of 3.34 inches. Each right isosceles triangular fin 30 extends from the inner surface 46 to an apex 0.5 inch away. Suitable joinery can be used; for example, tabs on the fins can be inserted into slots and the fins then welded to the respective support (either the shaft 22 or the sleeve 28). Although the fins 26, 26', 30, and 30' are triangular, one skilled in the art will recognize that the fins 26, 26', 30, and 30' can be elliptical, semicircular, or rectangular with an appropriate change of the conversion constant used to convert actual torque (dial readings) to yield stress.

FIGS. 4–6 show examples of adapters for measuring yield stress or determining yield point of cements and foamed cements for use in oil or gas wells, for example; however, the present invention in general can be used with other fluids and in applications other than in the oil and gas industry. Two other non-limiting examples include the food and cosmetic industries.

The present invention also provides a method of measuring yield stress. This method comprises operating a standard rotating viscometer, such as the type illustrated in FIG. 1, modified with a plurality of intermeshing fins such that a standard spring of the standard rotating viscometer responds to a torque that is related to yield stress and that is imposed by a stressed test material on a portion of the fins connected to the standard spring. More particularly, this method for using a Couette viscometer to determine yield point comprises: lowering a modified bob, connected to a standard Couette viscometer spring, and a modified sleeve into a test composition; rotating the modified sleeve at a low speed, three and six rpm are recommended; after steady torque is developed during rotation, the motor switch should be quickly turned off, allowing the torque dial to relax to a steady state asymptote, such as 18d in FIG. 3B. For most cement samples fifteen to thirty seconds is ample time for steady residual torque to be obtained. However, for cross-linked fracturing fluids, one hundred to three hundred seconds may be required for the torque decay to reach equilibrium. The torque results of this procedure should be similar to that of FIG. 3B. The YP of the sample composition is computed by inserting the 18d reading from FIG. 3B into Equation [8] below.

To modify a standard rotating viscometer for use in determining yield point, the present invention also provides for modifying a standard rotating viscometer by replacing a standard bob and a standard sleeve of the standard rotating viscometer with a modified bob and a modified sleeve. Disposed on the modified bob and modified sleeve are a plurality of intermeshing fins such that a standard spring of the standard rotating viscometer responds to a torque that is related to yield point and that is imposed by a stressed test material on the standard spring through connection of the standard spring to the modified bob. So, the conventional sleeve is replaced with a modified sleeve having a plurality of fins extending inwardly from an inner surface of the modified sleeve, and the conventional bob is replaced with a modified bob. The modified bob is connected to the standard Couette viscometer spring, and the modified bob has fins extending outwardly as described above. Thus, the modification is completed by replacing the conventional bob and the conventional sleeve without replacing the standard Couette viscometer spring.

In a particular example of a method of the present invention, a fluid sample to be tested (such as a drilling mud, a drill-in fluid, a cement or foamed cement, or an emulsion, for example) is loaded by lowering the modified bob 20 and modified sleeve 28 into the sample held in a suitable container of a type known in the art. The modified bob 20 and the modified sleeve 28 are connected in conventional manner into the rotating viscometer of FIG. 1 in place of the bob 4 and the sleeve 2, respectively. A speed of three rpm is selected and the motor of the motor drive 8 is turned on to rotate the modified sleeve 28 at that speed. Torque is measured via action of the spring 12 and the torque dial 14 imparted by movement of the modified bob 20 due to the stressed test fluid, and the torque readings are recorded. The motor is turned off, and residual torque is recorded for a sufficient time. For example, for an inelastic material like cement, fifteen to thirty seconds is long enough; for elastic fracturing gels, it may take up to three hundred seconds. Knowing the torque readings and the rotational speed, through a series of calibrations with Newtonian fluids of various viscosities and non-Newtonian fluids of various shear thinning indices, coefficients $k_1$ and $k_2$ can be determined, which allows accurate transformation of rpm versus torque data into shear stress versus shear rate data, namely:

Shear Rate (in units of 1/sec)=$k_1 \times$RPM, or $$\dot{\gamma} = k_1 (RPM) \qquad [6]$$

Viscosity (in Pa-sec)=$k_2 \times$Torque reading on the dial/RPM, or $$\eta = \left[ \frac{k_2(\text{Torque})}{RPM} \right] \qquad [7]$$

Shear Stress (in Pa)=$k_1 \times k_2 \times$Torque, or $$\tau = k_1 k_2 (\text{Torque}) \qquad [8]$$

The product of $k_1$ and $k_2$ can be referred to as a conversion constant. A more general method to determining proper values of $k_1$ and $k_2$ is as follows: a) establish that the volume average shear rate in the YPA device can be expressed as using Equation [6]; b) select an a priori viscosity model, such as those in Equations [1] through [5]; c) substitute the expression in Equation [7] above and solve for how torque versus rpm data can be analyzed to ascertain the rheological coefficients of the a priori model. For example, if the Bingham Plastic model is selected, then Equation [3] is set equal to Equation [7], and Equation [6] is substituted for the shear rate, resulting in the following expression where $k_3 = 1/k_2$:

$$\text{Torque} = \frac{[k_3(YP)]}{k_1} + k_3(PV)(RPM) \qquad [9]$$

Calibration tests can be conducted with fluids of known PV and YP, and then linear regression used to compute best fit "Intercept" and "Slope". Then the following equations can be used to compute $k_1$ and $k_3$:

$$k_3 = \left[ \frac{\text{Slope}}{PV} \right] \text{ and then} \qquad [10]$$

$$k_1 = \left[ \frac{\text{Slope}}{\text{Intercept}} \right] \left[ \frac{YP}{PV} \right] \qquad [11]$$

Once $k_1$ and $k_3$ are known for a given a priori viscosity model, such as Bingham Plastic in Equations [10] and [11], then linear regression of torque versus rpm data of unknown Bingham Plastic materials can be used along with $k_1$ and $k_3$ to compute PV and YP. If the fluid model is not known, it is best to use Equations [6] and [8] to convert torque versus rpm measurements directly to shear stress versus shear rate data. Therefore, the YPA device serves as an effective viscometer for fluids with particulates. Also, the YPA device is unique in that it directly measures the YP of a material, as described above.

Figure 7:
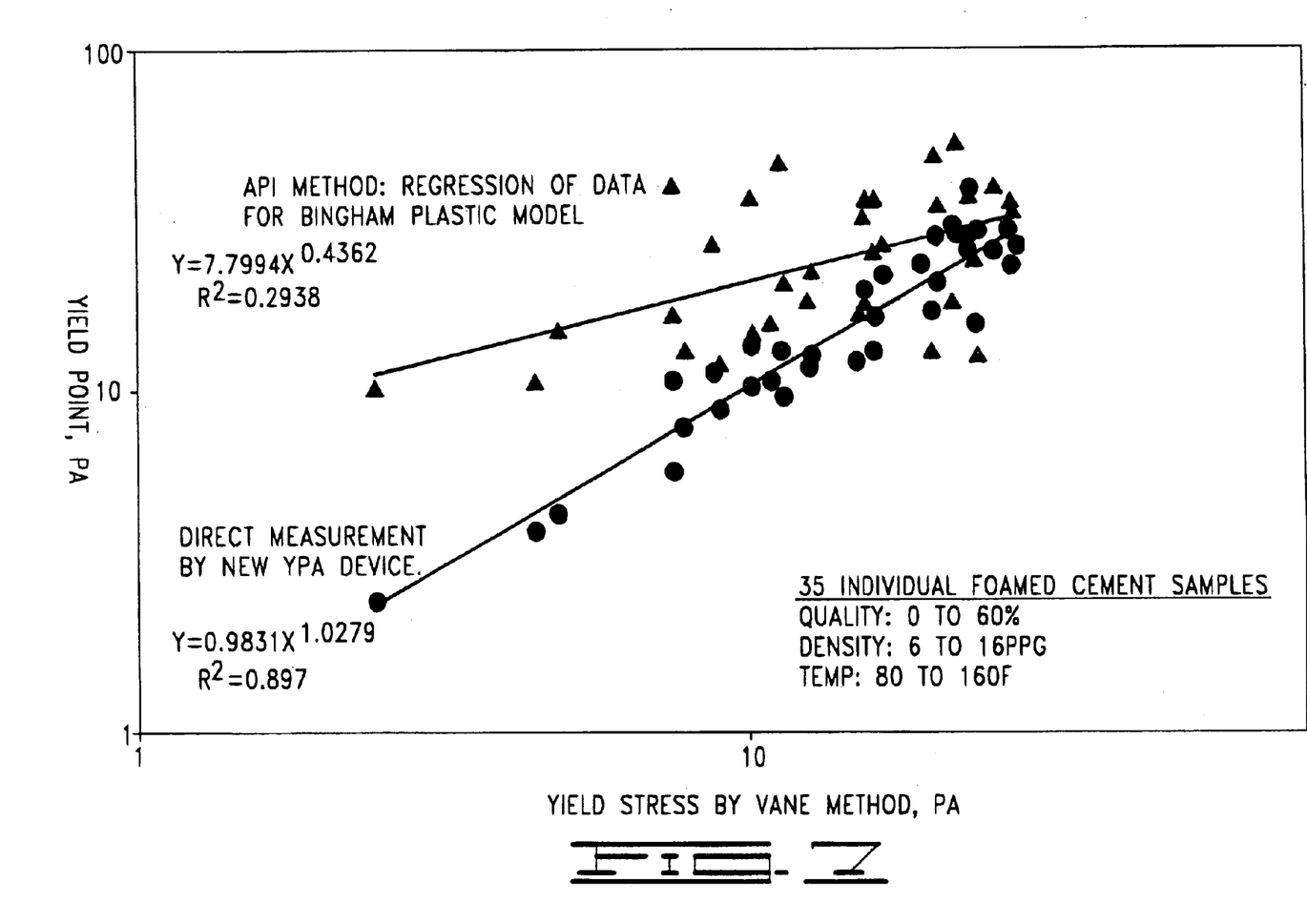
FIG. 7 illustrates the improved accuracy of using the present invention, referred to as a YPA device, to measure physical yield point, versus the results from a current methodology recommended by API (curve fitting shear stress-shear rate data using a priori viscosity model).

FIG. 7 illustrates the improved accuracy of using a YPA device to measure physical yield point, versus current methodology recommended by API (curve fitting shear stress versus shear rate data using an a priori viscosity model). The standard "vane method" (see page 138 of Steffe) was used to measure the physical YP of various types of foamed cements at various densities, quality (volume fraction of gas), and temperatures. Yield points of the same samples were also measured via the YPA device, described herein, and the API method defined for Bingham Plastics and plotted in FIG. 7. The solid triangles are the YPs measured via API regression method, while the solid circles are those obtained via the YPA device. Using the statistical parameter, R-squared of the linear regression as a direct measure of accuracy, note that the YPA device has an R-squared of 0.897, which is over 200% improved over the 0.294 observed for the API-regression fit method.

Figure 8:
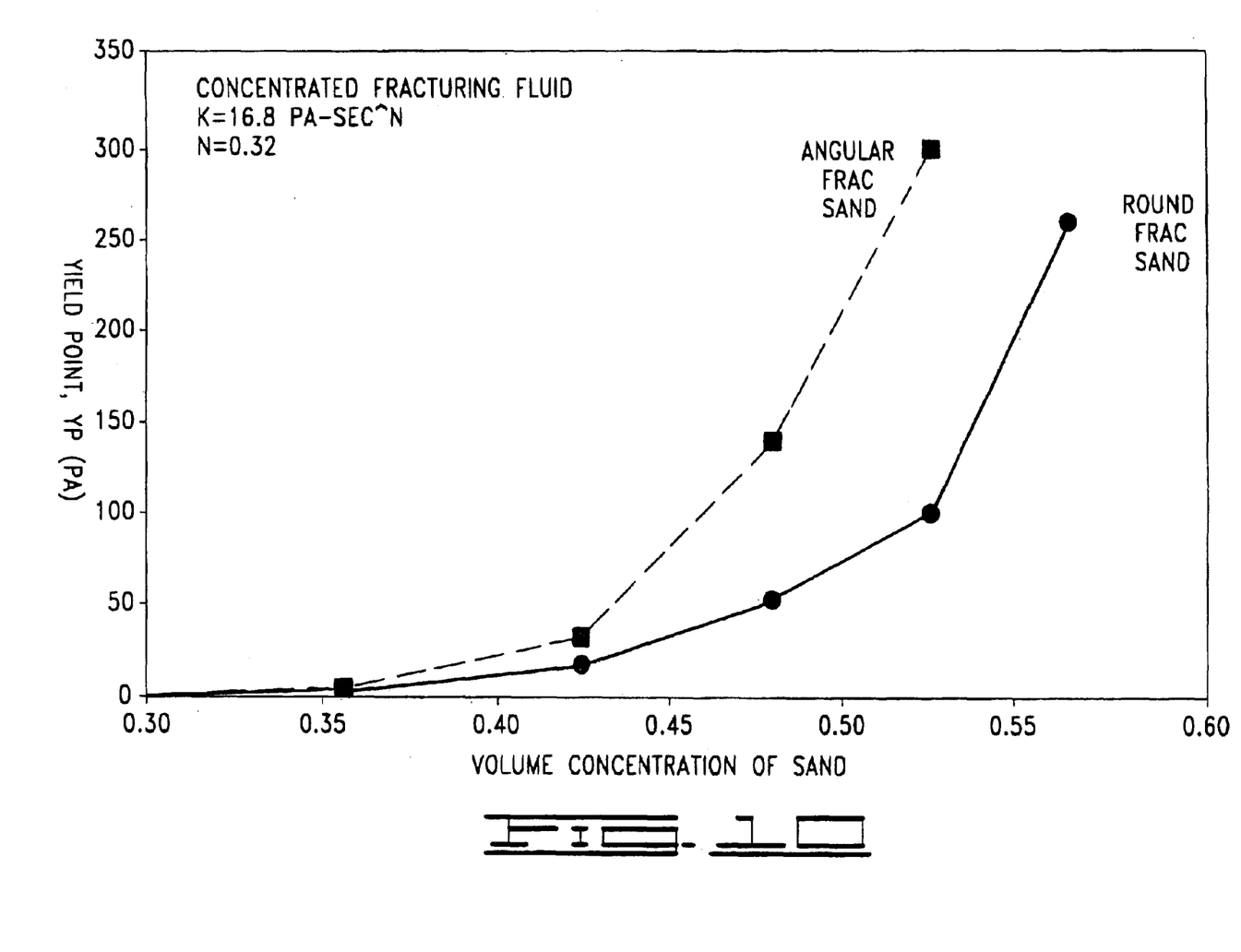
FIG. 8A illustrates the accuracy of using the YPA device as a "particulate viscometer adapter", particularly its ability to prevent errors due to centrifugal forces.
FIG. 8B illustrates the capability of the YPA device to serve as an effective means to measure rheology of highly concentrated particle laden slurries.

FIGS. 8A and 8B illustrate the utility of the YPA device as a particulate viscometer adapter. Note in FIG. 8A how the centrifugal effects of the conventional bob and sleeve Couette viscometer cause migration of particles away from the bob and thus lower viscosity readings. The viscosity data (solid circles) collected via the YPA device are more accurate in that the unique geometry of the fins of the modified bob and modified sleeve create a mixing action that suspends the particles and helps to maintain a homogeneous suspension. Centrifugal separation of the particles in conventional Couette viscometers may result in viscosities that are in considerable error by being of less magnitude (solid triangles) than would have been observed had the particulates been maintained in homogeneous suspension (solid circles). FIG. 8B illustrates how the YPA device has broad application in that it can accurately measure torque versus rpm data for particle laden fluids ranging from dilute (less than 1% volume/volume ratio) to "near close packing" (as much as 60% volume/volume ratio) concentrations. Typically, conventional bob and sleeve Couette viscometers often result in the centrifugal errors, illustrated in FIG. 8A, at moderate to low solids concentrations, whereas most conventional bob and sleeve viscometers will not even operate at particle concentrations approaching the "near close packing" concentrations.

FIG. 9 illustrates viscosity data collected via conventional bob/sleeve (B/S) and the YPA device. Plotted in FIG. 9 are viscosity data from four different linear fracturing gels collected by two methods: a) conventional bob and sleeve Couette viscometer; and b) the novel YPA device. The closed symbols are viscosity data from a conventional Couette (bob and sleeve) viscometer while the open symbols were obtained from a YPA prototype using Equations [6] and [7], for the same four shear thinning fracturing gels. Thus FIG. 9, showing that these data points for viscosity align, illustrates that when used as a standard viscometer, the YPA device has comparable accuracy to that of conventional bob and sleeve viscometers, when viscosities are sufficient to result in proper torque levels.

FIG. 10 illustrates the accuracy of the YPA device to directly measure the yield stress of various fluids, including those containing high concentrations of particles, compared with the conventional vane method commonly accepted by those trained in the art. Note in FIG. 10 that the YPA device is capable of detecting the differences in the effective yield stress of highly concentrated fracturing fluids created just by changes in particle shape. At concentrations normally encountered during fracturing (less than 0.30 volume/volume) the proppant laden uncross-linked fracturing fluid would normally not exhibit a detectable yield stress. However, as particle concentration approaches "near close packing" levels (greater than 0.40 volume/volume), the YPA device is capable of detecting the on-set of finite yield stresses, as well as detecting the effects of particle shape on the yield stress. For example, note how the yield stress for angular (non-spherical) frac sand at an approximate concentration of 0.53, is about three times that for the same concentration of round frac sand.

The adapted viscometer of the present invention not only functions as described above to directly measure yield stress or determine yield point of fluids with and without particulates, but it also can otherwise function in typical fashion to obtain measurements of characteristics or parameters obtainable with a conventional viscometer.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A method of measuring yield point of a fluid, comprising the steps of:
   providing a viscometer comprising:
      a bob having a plurality of fins attached thereto;
      a sleeve having a plurality of fins attached to an inner surface thereof; and
      a torque sensor for detecting torque applied to the bob;
   placing the bob and sleeve into the fluid;
   rotating the sleeve at a constant speed until the torque sensor indicates the torque has reached a first steady state value;
   stopping the rotation of the sleeve after the torque reaches the first steady state value;
   waiting until the torque sensor indicates the torque has decayed to a second steady state value; and
   multiplying the second steady state value of torque by a conversion constant to determine the yield point of the fluid.

2. The method of claim 1 wherein the step of rotating the sleeve at a constant speed comprises the step of rotating the sleeve at a constant low speed.

3. The method of claim 1 further comprising the step of performing a calibration test with calibration fluid having known rheological properties to determine the conversion constant.

4. The method of claim 1 wherein:
   the bob comprises a shaft, and the plurality of fins of the bob are axially spaced in groups along the shaft;
   the fins of the sleeve are circumferentially disposed around the inner surface of the sleeve; and
   the sleeve is configured to receive the bob within the sleeve such that the fins of the sleeve are disposed between the fins of the bob when the bob is received in the sleeve.

5. The method of claim 1 wherein:
   the bob comprises a shaft, and the plurality of fins of the bob are circumferentially disposed around the shaft;
   the fins of the sleeve are circumferentially disposed in groups around the inner surface of the sleeve; and
   the sleeve is configured to receive the bob within the sleeve such that the fins of the bob are disposed between the fins of the sleeve when the bob is received in the sleeve.

6. A method of measuring yield point of a fluid using a Couette viscometer having a substantially cylindrical bob, a rotating sleeve, and a spring adapted to respond to torque applied to the bob, comprising the steps of:
   replacing the bob with a modified bob comprising:
      a shaft; and
      a plurality of triangular fins circumferentially disposed around the shaft;
   replacing the rotating sleeve with a modified sleeve comprising a plurality of triangular fins circumferentially disposed about an inner surface of the modified sleeve;
   placing the modified bob and modified sleeve into the fluid;
   rotating the modified sleeve;
   sensing torque applied to the modified bob by the fluid responding to the rotating modified sleeve, wherein the torque applied to the modified bob displaces the spring; and
   computing the yield point of the fluid from the sensed torque.

7. The method of claim 6 wherein:
   the plurality of triangular fins of the modified bob comprise two axially spaced groups of triangular fins circumferentially disposed around the shaft; and
   the modified sleeve is configured to receive the modified bob within the modified sleeve such that a group of triangular fins of the modified sleeve is disposed between the two axially spaced groups of triangular fins of the modified bob.

8. The method of claim 6 wherein:
   the plurality of triangular fins of the modified sleeve comprise two axially spaced groups of triangular fins circumferentially disposed about the inner surface of the modified sleeve; and
   the modified sleeve is configured to receive the modified bob within the modified sleeve such that a group of triangular fins of the modified bob is disposed between the two axially spaced groups of triangular fins of the modified sleeve.

9. A method of measuring yield point of a fluid using a Couette viscometer having a substantially cylindrical bob, a rotating sleeve, and a spring adapted to respond to torque applied to the bob, comprising the steps of:
   replacing the bob with a modified bob having a plurality of fins attached thereto;
   replacing the rotating sleeve with a modified sleeve having a plurality of fins attached to an inner surface thereof;

placing the modified bob and modified sleeve into the fluid;

rotating the modified sleeve;

sensing torque applied to the modified bob by the fluid responding to the rotating modified sleeve, wherein the torque applied to the modified bob displaces the spring;

performing a calibration test with calibration fluid having known rheological properties to determine a conversion constant; and multiplying the sensed torque by the conversion constant to determine the yield point of the fluid.

10. The method of claim 9 wherein:

the modified bob comprises a shaft, and the plurality of fins of the modified bob are circumferentially disposed around the shaft;

the fins of the modified sleeve are circumferentially disposed in groups around the inner surface of the modified sleeve; and the modified sleeve is configured to receive the modified bob within the modified sleeve such that the fins of the modified bob are disposed between the fins of the modified sleeve when the modified bob is received in the modified sleeve.

11. A method of measuring yield point of a fluid, comprising the steps of:

providing a viscometer comprising:
a bob comprising:
a shaft; and
a plurality of triangular fins circumferentially disposed around the shaft;
a sleeve comprising a plurality of triangular fins circumferentially disposed about an inner surface of the sleeve; and
a spring adapted to respond to torque applied to the bob;

placing the bob and sleeve into the fluid;

rotating the sleeve;

sensing torque applied to the bob by the fluid responding to the rotating sleeve, wherein the torque applied to the bob displaces the spring; and computing the yield point of the fluid from the sensed torque.

12. The method of claim 11 wherein:

the plurality of triangular fins of the bob comprise two axially spaced groups of triangular fins circumferentially disposed around the shaft; and the sleeve is configured to receive the bob within the sleeve such that a group of triangular fins of the sleeve is disposed between the two axially spaced groups of triangular fins of the bob.

13. The method of claim 11 wherein:

the plurality of triangular fins of the sleeve comprise two axially spaced groups of triangular fins circumferentially disposed about the inner surface of the sleeve; and the sleeve is configured to receive the bob within the sleeve such that a group of triangular fins of the bob is disposed between the two axially spaced groups of triangular fins of the sleeve.

14. A method of measuring yield point of a fluid, comprising the steps of:

providing a viscometer comprising:
a bob having a plurality of fins attached thereto;
a sleeve having a plurality of fins attached to an inner surface thereof; and
a spring adapted to respond to torque applied to the bob;

placing the bob and sleeve into the fluid;

rotating the sleeve;

sensing torque applied to the bob by the fluid responding to the rotating sleeve, wherein the torque applied to the bob displaces the spring;

performing a calibration test with calibration fluid having known rheological properties to determine a conversion constant; and multiplying the sensed torque by the conversion constant to determine the yield point of the fluid.

15. The method of claim 14 wherein:

the bob comprises a shaft, and the plurality of fins of the bob are circumferentially disposed around the shaft;

the fins of the sleeve are circumferentially disposed in groups around the inner surface of the sleeve; and the sleeve is configured to receive the bob within the sleeve such that the fins of the bob are disposed between the fins of the sleeve when the bob is received in the sleeve.

16. Apparatus for measuring yield point, comprising:

a bob comprising:
a shaft; and
a plurality of triangular fins circumferentially disposed around the shaft; and a sleeve comprising a plurality of triangular fins circumferentially disposed about an inner surface of the sleeve;

wherein:

the sleeve is configured to receive the bob within the sleeve such that the triangular fins of the sleeve intermesh with the triangular fins of the bob when the bob is received in the sleeve;

the sleeve is adapted to rotate about the bob; and the yield point of a fluid is calculated from torque applied to the bob by the fluid when the sleeve is rotated.

17. The apparatus of claim 16 wherein:

the plurality of triangular fins of the bob comprise two axially spaced groups of triangular fins circumferentially disposed around the shaft; and the plurality of triangular fins of the sleeve comprise a group of triangular fins disposed between the two axially spaced groups of triangular fins of the bob.

18. The apparatus of claim 16 wherein:

the plurality of triangular fins of the sleeve comprise two axially spaced groups of triangular fins circumferentially disposed about the inner surface of the sleeve; and a group of triangular fins of the bob is disposed between the two axially spaced groups of triangular fins of the sleeve.

19. The apparatus of claim 16 further comprising:

a motor connected to the sleeve; and a torque sensor connected to the bob, comprising:
a spring; and
a torque dial.

20. The apparatus of claim 19 wherein:

the torque sensor measures the torque applied to the bob by the fluid when the sleeve is rotated by the motor; and the yield point of the fluid is calculated by multiplying the torque indicated by the torque dial by a conversion constant.

* * * * *